(12) United States Patent
Goupy et al.

(10) Patent No.: US 6,824,797 B2
(45) Date of Patent: Nov. 30, 2004

(54) METHOD FOR EXTRACTING, FRACTIONATING AND PURIFYING POLYPHENOLIC COMPOUNDS ORIGINATING FROM FRESH PLANT SORTING DEVIATIONS USING A HIGH ADSORPTION AND ELUTION PERFORMANCE RESIN

(75) Inventors: Pascale Goupy, Gargas (FR); Marie-Josephe Amiot-Carlin, Montfavet (FR); Jean-Louis Escudier, Armissian (FR); Michel Mikolajczak, Gruissan (FR); Michel Martin, Nevian (FR)

(73) Assignees: Institut National de la Recherche Agronomique INRA, Paris (FR); SCALIME France, Lyons (FR)

( * ) Notice: Subject to any disclaimer, the term of this patent is extended or adjusted under 35 U.S.C. 154(b) by 0 days.

(21) Appl. No.: 10/077,225

(22) Filed: Feb. 15, 2002

(65) Prior Publication Data

US 2002/0187207 A1 Dec. 12, 2002

(30) Foreign Application Priority Data

Feb. 15, 2001 (FR) .......................... 01 02096

(51) Int. Cl.⁷ .................... A61K 35/78; A61K 31/35; A61K 31/05
(52) U.S. Cl. ................ 424/764; 424/725; 514/456; 514/732
(58) Field of Search ................. 424/764, 725, 424/754; 514/456, 732, 734, 738; 426/481, 489

(56) References Cited

U.S. PATENT DOCUMENTS

| 4,800,339 A | 1/1989 | Tanimoto et al. ........... 330/253 |
| 4,910,182 A | 3/1990 | Hums et al. ................. 502/402 |
| 5,141,611 A | 8/1992 | Ford ......................... 204/182.4 |
| 5,853,728 A | * 12/1998 | Tanabe et al. |
| 5,856,429 A | 1/1999 | Michos ....................... 528/332 |
| 5,994,413 A | 11/1999 | Tanabe et al. .............. 514/732 |
| 6,238,673 B1 | * 5/2001 | Howard |
| 2001/0014669 A1 | * 8/2001 | Bok et al. |

FOREIGN PATENT DOCUMENTS

| EP | 0728189 | 8/1996 |
| FR | 2307779 | 11/1976 |
| FR | 2712206 | 5/1995 |
| JP | 06088063 | * 3/1994 |
| JP | 09002917 | * 1/1997 |
| JP | 10194907 | * 7/1998 |
| SU | 483981 | * 12/1975 |

OTHER PUBLICATIONS

Mastsuo et al. 1983. Kagoshima Daigaku Nogakubu Gakugutsu Hokoku. vol. 33, pp. 21–28, CAPLUS Abstract enclosed.*

Goupy et al., "Antioxidant composition and activity of barley (*Hordeum vulgare*) and malt extracts and of isolated phenolic compounds," *J. of the Science of Food and Agriculture*, 79:1625–1634, 1999.

* cited by examiner

*Primary Examiner*—Christopher R. Tate
(74) *Attorney, Agent, or Firm*—Fulbright & Jaworski L.L.P.

(57) ABSTRACT

This invention relates to a method for extracting, fractionating and purifying polyphenolic compounds originating from plants, wherein the purification is performed by adsorption on an adsorbing styrene-divinyl benzene resin, followed by the elution of the polyphenolic compounds.

40 Claims, 4 Drawing Sheets

DHC: Hydroxycinnamic acids; Fols: Flavonols

Q: quercetine; QMG: quercetine monoglucoside; QDG: quercetine diglucoside

US 6,824,797 B2

METHOD FOR EXTRACTING, FRACTIONATING AND PURIFYING POLYPHENOLIC COMPOUNDS ORIGINATING FROM FRESH PLANT SORTING DEVIATIONS USING A HIGH ADSORPTION AND ELUTION PERFORMANCE RESIN

CROSS REFERENCE TO RELATED APPLICATIONS

The present application claims priority to French Application No. 01/02096 filed 15 Feb. 2001, the entire text of which is specifically incorporated by reference herein without disclaimer.

FIELD OF THE INVENTION

This invention relates to a method for extracting, fractionating and purifying compounds originating from leafy edible plants of the Compositae family or bulb plants of the Liliaceae family or from sorting deviations of fresh plants in order to obtain an extract comprising polyphenolic compounds.

More particularly, the invention provides a method for extracting, fractionating and purifying polyphenolic compounds, wherein the purification is performed by polyphenolic compound adsorption on an adsorbing resin, followed by the elution of the compounds retained on the resin.

According to the invention, it is meant by extract comprising phenolic compounds a product having a polyphenolic compound minimum content equal to or higher than 30% based on the dry weight.

According to the invention, it is meant by purification the recovery or the selection of the extracted phenolic compounds.

BACKGROUND OF THE INVENTION

Methods for extracting and purifying the polyphenolic compounds in plant materials using an adsorbing resin are known in the prior art.

U.S. Pat. No. 5,994,413 relates to a method for extracting polyphenolic compounds from Rosaceae fruit, such as apples, pears, peaches and related fruits. This patent more particularly discloses a polyphenolic compound isolation and purification method from fruit using juice extraction from peeled or non peeled fruit, crushing the fruit, followed by centrifugation and recovery, followed with the passage of the juice thus obtained on a resin able to selectively retain the phenolic compounds and finally the elution of the polyphenols retained on the resin so as to obtain a powder comprising phenolic compounds. This patent mentions several adsorbants, such as synthetic styrene-divinyl benzene resins, anion exchange resins or silica gels on which are chemically fixed the octadecyl groups, the elution of the polyphenols adsorbed on these resins being performed by adding an alcohol solution, such as ethanol.

U.S. Pat. No. 5,141,611 discloses a method allowing to eliminate the polyphenolic substances contained in a solution, and, optionally, to recover them using a polyamid resin on which the polyphenols are adsorbed.

U.S. Pat. No. 5,856,429 relates to a method for removing polyphenols from liquids, wherein the polyphenols are retained on an amid resin. This patent also discloses other types of polyphenol adsorbing medium, such as Nylon or polyvinylpolypyrrolidone (PVPP).

U.S. Pat. No. 4,910,182 discloses a method for stabilizing drinks containing polyphenols wherein an adsorbing polyvinylpolypyrrolidone (PVPP) medium is used. Such a method is particularly adapted for elimination of polyphenolic compounds from beer.

U.S. Pat. No. 4,800,339 relates to a method for eliminating polyphenols from vegetable origin drinks such as beers, wines and fruit juices, using a N-substituted polyamid based adsorbing resin.

These methods, however, have the disadvantage that they use resins that either have a high adsorption performance or a high elution performance, but that do not simultaneously have both a high adsorption performance and a high elution performance.

SUMMARY OF THE INVENTION

An object of the present invention therefore is to provide a method for extracting, fractionating and purifying polyphenolic compounds, removing the prior art drawbacks.

In particular, an object of the present invention is to provide a method for extracting, fractionating and purifying comprising a step for extracting the polyphenolic compounds originating from leafy edible plants of the Compositae family or bulb plants of the Liliaceae family or plants of the rosaceous family or the sorting residues thereof, or from sorting deviations of fresh plants, an adsorption step followed with an elution step of such compounds using a resin having particular physical features, giving it a high adsorption ability of the polyphenolic compounds and a high elution ability.

Another object of said invention is to provide a product comprising polyphenolic compounds using the method of the invention.

Another object of the invention is to provide the use of a product such as defined here-above for making cosmetics and/or pharmaceutical compounds and/or food ingredients.

The aims of the present invention are therefore achieved by a method for extracting, fractionating and purifying polyphenolic compounds originating from leafy edible plants of the Compositae family or bulb plants of the Liliaceae family, or from sorting deviations of fresh plants, comprising the following steps of:

a) extracting the polyphenolic compounds in order to obtain a raw plant material extract, b) adsorbing on an adsorbing resin the polyphenolic compounds contained in the raw extract, c) eluting the polyphenolic compounds retained on the resin in order to obtain a purified extract, and d) concentrating, optionally followed by drying, the purified extract in order to obtain a product comprising polyphenolic compounds, wherein the resin is a styrene-divinyl benzene resin having the following physical features:

1) pores with an average size in the range from 50 to 110 angstroms, preferably from 60 to 100 angstroms, 2) a surface area equal to or higher than 800 $m^2/g$, preferably equal to or higher than 880 $m^2/g$, giving the resin an organic particle high adsorption ability, 3) a pore volume higher than 1 ml/g, and preferably equal to or higher than 1.4 ml/g.

Preferably, the resin according to the invention has the following physical features:

1) pores with an average size in the range from 80 to 110 angstroms, preferably from 88 to 92 angstroms, and more preferably about 90 angstroms, 2) a surface area equal to or higher than 1000 m²/g, preferably equal to or higher than 1200 m²/g,
3) a pore volume equal to or higher than 2 ml/g, and preferably equal to or higher than 2.4 ml/g.

The food solvent is preferably ethanol or methanol.

The elution should be easy, fast and as thoroughly as possible in order not to dilute the extract, and, consequently, the global performance of the method.

The purified extract, or eluate, is generally concentrated and a product comprising polyphenolic compounds is obtained, the extract being able to be spray-dried or freeze-dried.

The resin of this invention preferably has the formula (I):

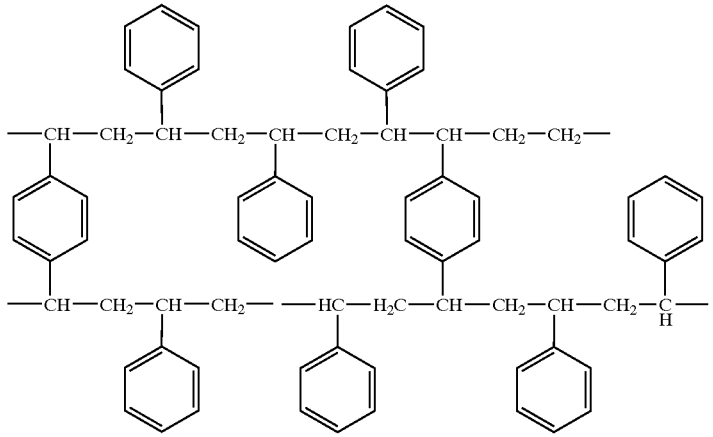

(I)

DESCRIPTION OF THE ILLUSTRATIVE EMBODIMENTS

Figure 1:
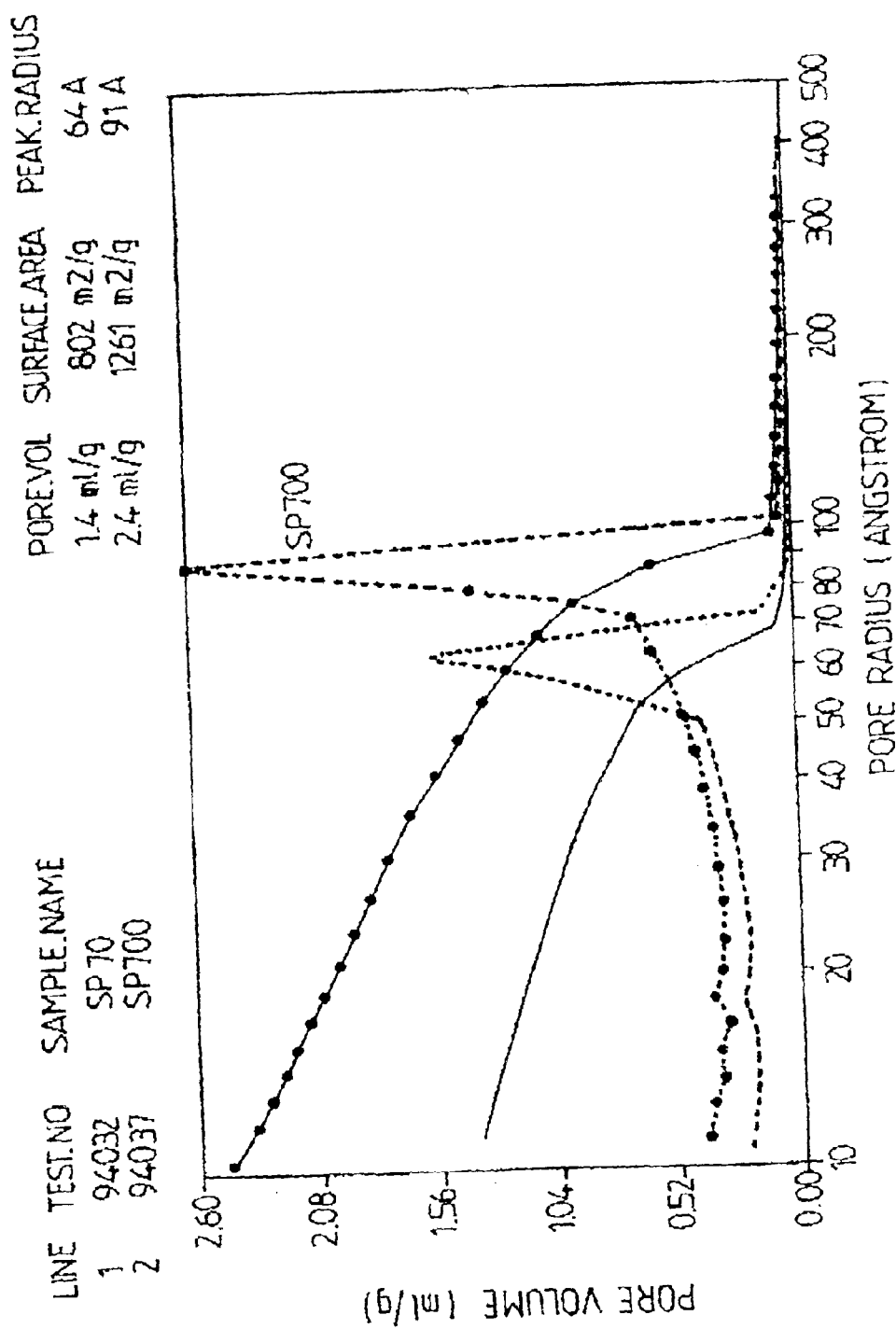
FIG. 1 illustrates pore distribution for the resins according to the invention.

The pore distribution depending on their size is shown on FIG. 1, for two resins according to the invention.

The resins according to the invention adsorb the polyphenolic compounds contained in the plants, but do not show any or little affinity with a whole range of molecules and solutes also contained in these same plants, which are partly eliminated, such as dissolved salts, sugars, polyosides, cations, anions, nitrates and nitrites.

Plants are generally plants or fruit. More particularly, within the scope of the present invention, the polyphenolic compounds are in the plant tissues of the edible plants.

It is meant by edible plants any plant for use in cooking.

The most preferred edible plants are leafy edible plants of the Compositae family or bulb edible plants of the Liliaceae family.

Examples of plants of the Compositae family include lettuce, endive and more particularly, escarole and curly endive.

Amongst the various lettuce species, one can mention, for example, cos lettuce, batavia, iceberg lettuce etc.

Examples of the bulb plants of the Liliaceae family include onion, garlic, leek and shallot.

Once selectively fixed, the molecules to be enhanced, i.e. the polyphenolic compounds, are eluted with a solvent, preferably a food solvent.

It is meant by food solvent, within the present invention, any solvent adapted for the preparation of products intended for human or animal food.

An illustration of a resin according to the invention include the styrene divinyl benzene resins, available from RESINDION company under the trade names SP70 and SP700.

The adsorbing resins according to the invention are very selective towards polyphenolic compounds and have a strong elution capacity with food solvents such as methanol or ethanol.

In particular, the adsorption rate of the polyphenolic compounds on the resin is equal to or higher than 80% and the elution rate of the polyphenolic compounds is equal to or higher than 60%.

It is meant by adsorption rate of the polyphenolic compounds, the ratio of the quantity of polyphenolic compounds fixed on the resin to the quantity of polyphenolic compounds contained in the raw extract.

Similarly, it is meant by elution rate, the whole performance of the method, i.e. the ratio of the quantity of polyphenolic compounds contained in the purified extract (or eluate) to the quantity of the polyphenolic compounds contained in the raw extract.

The extraction of the phenolic compounds generally comprises quickly heating the plant from a room temperature of 25° C. up to a temperature as high as 105° C., in order to obtain a hot exudation juice and a must of cooled exuded cooked plants, the exudation juice constituting at least partially the raw extract.

A quick heating is preferably carried out in the absence of oxygen from the air for blocking the enzyme activity and the protection of the treated plant materials against possible oxidative or hydrolytic damage.

Advantageously, heating is carried out in a period of time ranging from one to fifteen minutes without maceration.

In order to improve the extraction, i.e. to obtain a higher quantity of polyphenolic compounds in the raw extracts, while maintaining the quality of the extracted compounds, the quick heating may be followed by a substantially immediate vacuum step of the plant, leading to the vaporization of a portion of the plant, this step being carried out at a pressure in the range from $10^3$ to $2\times10^4$ Pa.

The vacuum step is required when the polyphenolic compounds are present in edible plants of the Liliaceae family, including onion, for which the extraction of the polyphenolic compounds is difficult.

On the other hand, when the plants are of the Compositae family, and more particularly lettuces, the vacuum step is useful but not necessary.

The extraction of the polyphenolic compounds, more particularly the quick heating and vacuum steps of the plant material, have been disclosed in the European patent EP-0728189 and the French patent FR-9313286.

Several heating procedures can be used. Preferably, the plant heating is carried out by circulating juice originating from the treated plants or vapour on the plants.

Other methods, continuous or batch methods, can also be used. One can mention for example micro-wave heating, induction heating, ohmic heating, vessel batch heating or heating from a heat exchanger.

Examples of heat exchangers include for example tubular or plate thermal exchangers, scraped surface exchangers which allow a direct supply of calories to the plants, Corugais heat exchangers, and coaxial heat exchangers.

The purified extract may be used in a dry or a liquid state, but it is preferably used in a dry state.

According to the invention, the purified extract may be spray-dried or freeze-dried.

According to the invention, the purified extract has a polyphenolic compound content equal to or higher than 30%.

If the edible plants from which the polyphenolic extracts are extracted are lettuces, flavonols represent at the most 25% of the polyphenolic compounds and hydroxycinnamic acid esters represent at least 50% of the polyphenolic compounds, based on the total weight of the dry purified extract.

The hydroxycinnamic acid esters are i.e. caffeic acid derivatives comprising tartaric acid esters with monocaffeoyltartaric acid, isomers of dicaffeoyltartaric acid, 5'-caffeoylquinic acid (or chlorogenic acid), 3'-5'dicaffeoylquinic acid (or isochlorogenic acid), caffeoylmalic acid and feruloylquinic acid.

The flavonols comprise kaempferol-3-glucoside (kaempferol or luteoline), kaempferol-3-glucuronide, kaempferol-3-O-malonylglucoside, quercetine-3-glucuronide, quercetine-3-O-malonylglucoside and kaempferol-malonylglucoside derivatives.

On the other hand, if the edible plants are onions, the flavonols represent at least 80%, and in some cases at least 90%, of the polyphenolic compounds based on the total weight of the dry purified extract.

They comprise, for example, quercetine-3,4'-diglucoside, quercetine-4'-monoglucoside, quercetine, the isorhamnetine-3,4'-diglucoside and isorhamnetine-4'-monoglucoside.

The antiradical properties of the lettuce and onion purified extracts are assessed for their ability to neutralise the DDPH radical, according to the method described in the paper by P. Goupy, M. Hugues, P. Boivin and M. J. Amiot, Journal of the Science of Food and Agriculture, 1999, 79, pages 1625–1634.

The antiradical activity is defined as being the $1/Cl_{50}$ ratio, where $Cl_{50}$ is defined as the quantity of purified product required for the 50% reduction of the DDPH quantity present at an initial concentration of $6\times10^{-5}$ mole.$l^{-1}$.

The higher the $1/Cl_{50}$ ratio value, the higher the extract antiradical activity.

According to the invention, the lettuce extract has an antiradical activity defined by a $1/Cl_{50}$ ratio equal to or higher than 0.2 and the onion extract has an antiradical activity defined by a $1/Cl_{50}$ ratio equal to or higher than 0.12, for a polyphenolic compound content equal to or higher than 30%.

The products obtained according to the invention may be used for producing cosmetics and/or pharmaceutical compounds and/or food ingredients.

The following examples illustrate the invention, without however limiting the scope thereof.

In the examples, unless otherwise specified, all the quantities are expressed in weight fraction based on the polyphenolic compound quantity contained in a raw extract.

1. Raw Materials

Extraction of Polyphenolic Compounds Contained in Lettuces and Onions

Lettuce and onion extracts have been prepared during the extraction step of the method according to the invention, which is disclosed in the European patent EP-0728189 and in French patent FR-9313286.

Figure 2:
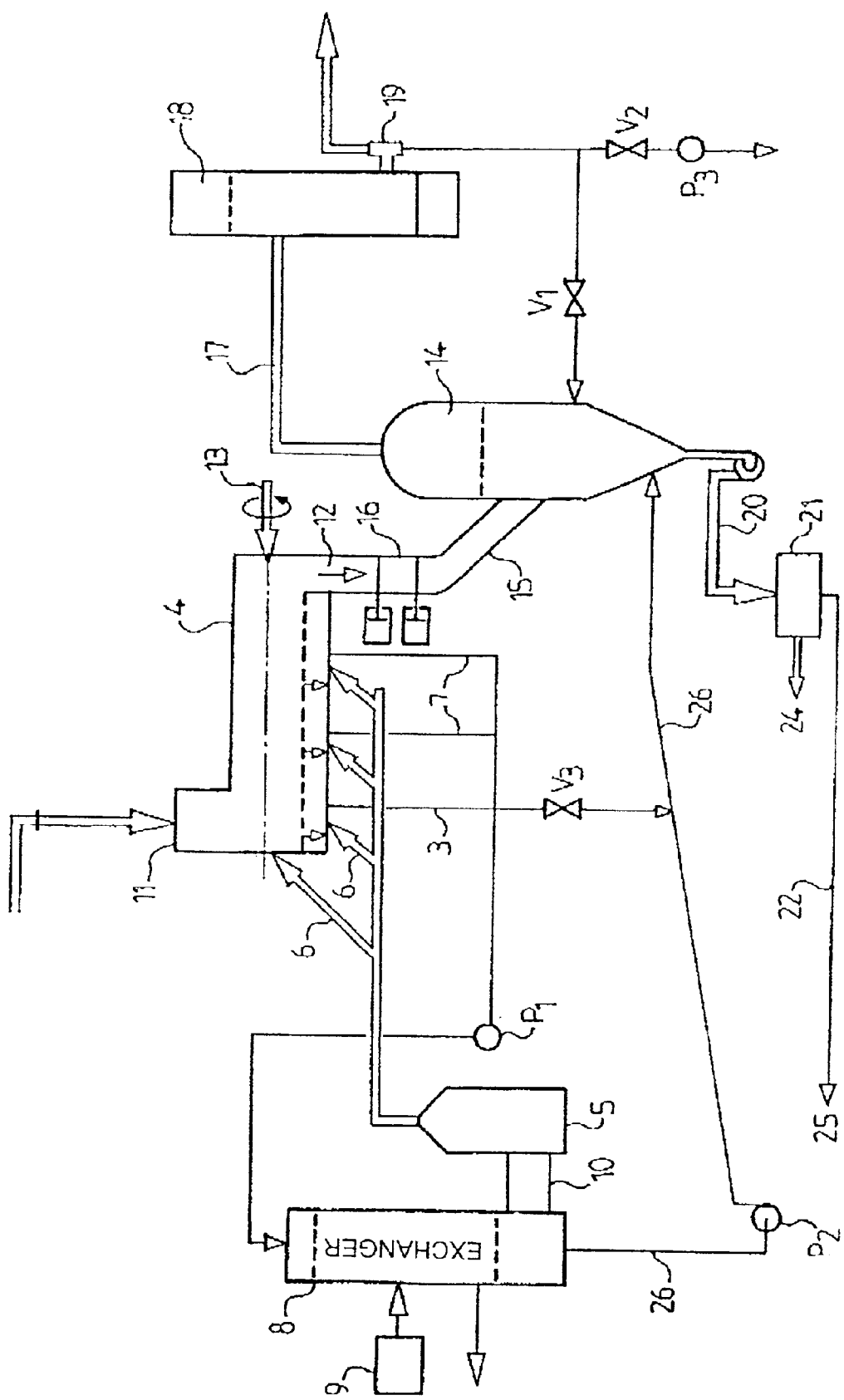
FIG. 2 shows a device for carrying out the method of the invention.

FIG. 2 shows a device for carrying out this method.

The material treated using this extraction method is made from lettuce and onion sorting deviations.

The method can be applied to fresh plant sorting deviations of any nature.

In the method shown in FIG. 2, the fresh plant (or plant material) sorting deviations are brought to a heating room 4.

The plant material heating is carried out at a temperature precisely controlled within the temperature range from 25 to 105° C., while avoiding the presence of air which could lead to oxidative damage.

The plant material heating in the heating room 4 can be carried out using any appropriate means. For example, one can supply in room 4 biological condensing vapour, originating from juice or condensates generated from the method. This vapour originates from the device 5, through ducts 6.

The condensates and the dripping or exudation juices are collected from the heating room 4 and supplied, through ducts 3 and 4 and a pump P1, into an heat exchanger 8. It can also be contemplated to transfer juice coming from the press (reference 22) into the heat exchanger 8. This alternative is not shown in FIG. 2.

The duct 3 is preferably connected to duct 26 by means of a valve V3. Thus, when the ducts 7 transfer the condensates and juices in sufficient quantity, the valve V3 is opened and the condensates and the juices from the duct 3 are directly transferred into the releasing chamber 14. This makes it possible to obtain a better energetic performance in that the condensates and the juices supplied by the duct 8 are cooler than those of the duct 7.

In the opposite condition, the valve V3 is closed and all the condensates and juices recovered in the ducts 3 and 7 are supplied to the heat exchanger 8.

A vapour generator 9 is connected to the heat exchanger 8 which is preferably a scraped surface heat exchanger transferring vapour to the device 5 by appropriate means 10.

This device makes it possible to avoid heating by an exogenous water vapour coming directly from a boiler room.

The heating time can be set, making it possible to heat either all the plants, or the film of the plants as it is the case with onions, or elsewhere a circumferential portion of said plants. This allows to control the extraction level of the various polyphenolic compounds present in these plant materials.

The heating time is relatively short. It is below 5 minutes, and preferably equal to about 3 minutes in the extraction of polyphenolic compounds contained in these lettuces. For the extraction of the onion polyphenolic compounds, the heating time is less than 15 minutes, and preferably equal to about 10 minutes.

The plant material is heated at a temperature ranging from a room temperature of 25° C. up to a temperature as high as 105° C., depending on the nature of the plants for lettuces and onions, the heating temperature is preferably higher than or equal to 90° C.

In FIG. 2, the plant material is transferred from the inlet of the heating chamber 4 as far as the outlet 12, through screws, carrying perforated troughs which are adapted for accommodating a determined quantity of material. The screws rotate about an axis 13. The rotation speed, the settable layer height, the screw length as well as the heating belt width define the flow rate and the dwell time of the heated products.

The heated plant material is transferred from the outlet 12 of the heating room 4 up to a releasing chamber 14 by means of a duct 15. The latter is provided with an airlock or a pump 16, preferably substantially sealed, so as to avoid vapour leakage.

The releasing chamber 14 is connected by appropriate means 17 to a condenser 18 which is in turn connected to a vacuum device 19.

The preheated material is substantially immediately evacuated. The absolute pressure inside the releasing chamber 14 lies within the range from absolute $10^3$ to $2\times10^4$ absolute Pa. The pressure value is selected depending on the nature of the plants. For example, with polyphenolic compounds extracted from onions, the absolute pressure in the releasing chamber is $12\times10^3$ absolute Pa, while it is advantageous to use a relatively lower absolute pressure in the order of $6\times10^3$ Pa in the case of polyphenolic compounds extracted from lettuces.

The vacuum in the chamber 14 is obtained by condensation of the vapours emitted through the condenser 18.

This very quick vacuum step results in a self vaporization of the liquid fractions of plant material which disintegrates the structure of the previously heated plant material. This makes it possible to increase the vacuum step of different compounds and in particular of the polyphenolic compounds.

This effect is all the more important as the difference between the heating temperature of the plant material and that resulting from the vacuum step is important as well.

The treated plant material is then removed from the releasing chamber 14 by appropriate means 20. The product leaving the releasing chamber 14 is a plant material sludge.

It is should be noted that such a sludge leaves the releasing chamber 14 at a relatively low temperature, in the order of 20 to 25° C., when the vacuum present in this chamber is very high (absolute pressure in the order of $2\times10^3$ Pa) and that the plant material has been heated at an appropriate temperature.

The sludge can be allowed to diffuse.

The sludge is squeezed in the device 21, so as to obtain a juice, also called raw pressing juice that flows through the duct 22.

The sludge squeezed in 24 is recovered, which is a pressing cake made of plant material.

If only a juice is to be obtained from the sludge, all the juice obtained using the method is recovered.

If a fermented juice is to be obtained, (in the case of onion, for example), the sludge coming from the releasing chamber 14 is fermented, after an enzyme and yeast treatment of this sludge.

It should also be noted that the juice obtained at the heat exchanger outlet 8 is supplied to the releasing chamber 14, by means of duct 26 and pump P2.

The vapour originating from the vacuum step is recovered, at the condenser outlet 18, as aromatic condensates. These can be transferred from condenser 18 towards the releasing chamber 14, the valve V1 being then opened and the valve V2 closed, which makes it possible to reconstitute a sludge having an identical weight to that of the raw plant material. It can also be contemplated to transfer the condensates present in the condenser 18 towards the outside of the device, by means of the pump P3. In this condition, the valve V1 is closed and the valve V2 is opened. This alternative method allows to carry out a controllable pre-concentration of the sludge.

In this alternative, the aromatic condensates can be treated to concentrate the flavours and to separate water.

The raw pressing juice and the exudation juice, containing the polyphenolic compounds to be enhanced, are gathered in order to constitute the raw juice or the raw plant extract.

When the method according to the invention is carried out with the device shown in FIG. 2, the raw material is treated continuously.

The method that has just been described makes it possible to obtain raw extracts of plants the polyphenolic compounds of which are fractionated and purified using a high performance adsorption and elution resin.

2. Methods of Measurement

The resin R used in the method according to the invention is a styrene-divinyl benzene resin having the formula (I) and the physical features thereof are shown in table 1.

TABLE 1

| Physical features | Resin R |
|---|---|
| Pore average size (angstroms) | 90 |
| Surface area (m²/g) | 1200 |
| Pore volume (ml/g) | 2.4 |

Polyphenolic Compound Quantification

The polyphenolic compounds are analysed by HPLC and quantified by external standardisation.

For lettuce extracts, the various contents are expressed in equivalent chlorogenic acid grams for hydroxycinnamic acid esters (EAC) and in equivalent quercetine grams for flavonols (EQ).

For onion extracts, the contents are expressed in equivalent quercetine-4'-monoglucoside or in equivalent quercetine-3,4'-diglucoside for the compounds identified as such or in equivalent quercetine for the other flavonols.

This method has the advantage, beside quantifying each compound present in the extract or in the analysed solution, to check the presence of all polyphenolic compounds.

The quantification is carried out for:
the raw extracts deposited on the resins,
the solutions eluted during the loading step and washing step with water of the resin preceding the elution as such, in order to check the polyphenolic compound loss during this step, the polyphenolic compounds adsorbed on the resin, and the purified extracts.

The ratio of the quantity of phenolic compounds adsorbed on the resin R to the quantity of polyphenolic compounds contained in the raw extract deposited on this resin is the adsorption rate $T_A$ of the phenolic compounds on the resin.

Similarly, the ratio of the polyphenolic compound quantity contained in the purified extract to the quantity of the polyphenolic compounds contained in the raw extract is the rate $T_E$ of the polyphenolic compounds recovered after the methanol elution. This ratio is the whole yield of the purification method.

Finally, the $T_{NE}$ rate of non elutable polyphenolic compounds that are fixed on the resin is the ratio of the polyphenolic compound quantity adsorbed on the resin and not eluted during the methanol elution step or eluted during the washing step with water or during the loading step, and the quantity of polyphenolic compounds contained in the extract deposited on the resin.

The adsorption rate $T_A$ on the phenolic compound resin is the sum of the $T_E$ and the $T_{NE}$ rates.

EXAMPLE 1

Lettuce Extract Purification

The raw lettuce extracts have been purified using respectively the method according to the invention.

The lettuce raw extracts are deposited on the resin R (load). The used resin volume is 25 ml, i.e. 1 BV (Bed Volume). After washing with a water volume of 125 ml (i.e. 5 BV), the polyphenolic compounds are eluted with 80 ml of methanol, i.e. 3.2 BV. A PE purified extract is obtained.

The solution eluted during the loading step and that eluted during the water washing of the resin are gathered and brought to a volume of 350 ml, the nature and the polyphenolic compound quantity of which are also analysed in order to quantify the polyphenolic compound loss during this step.

The polyphenolic compound quantity contained in the PE purified extract is measured. This measure is shown in FIG. 3.

Figure 3:
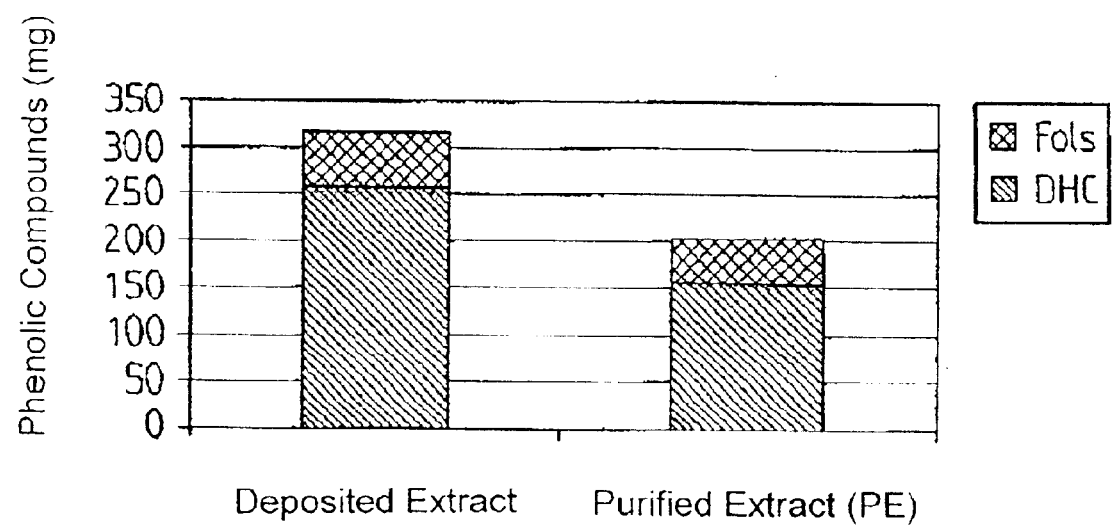
FIG. 3 shows polyphenolic compound contents.

FIG. 3 shows that the deposited raw extract contains 317 mg of polyphenolic compounds and the PE purified extract contains 199 mg of phenolic compounds. No qualitative difference is observed between the deposited extract and the purified extract: these extracts contain hydroxycinnamic acids and flavonols.

The obtained values for the $T_A$, $T_E$ and $T_{NE}$ rates, as well as the quantity of the polyphenolic compounds fixed by ml of resin are shown in table 2.

TABLE 2

| | Resin R |
|---|---|
| $T_A$ [%] | 87 |
| $T_E$ [%] | 63 |
| $T_{NE}$ [%] | 24 |
| Polyphenol quantity fixed on the resin [mg/ml of resin] | 11.1 |

EXAMPLE 2

Onion Extract Purification

The onion raw extracts are deposited on resin R. After water washing (125 ml, i.e. 5 BV), the compounds are eluted with 100 ml of methanol (i.e. 4 BV). A PE purified extract is obtained.

The solutions eluted during the loading step and the water washing of resin are gathered and brought to a volume of 300 ml, for quantifying the polyphenolic compound loss during this step.

Figure 4:
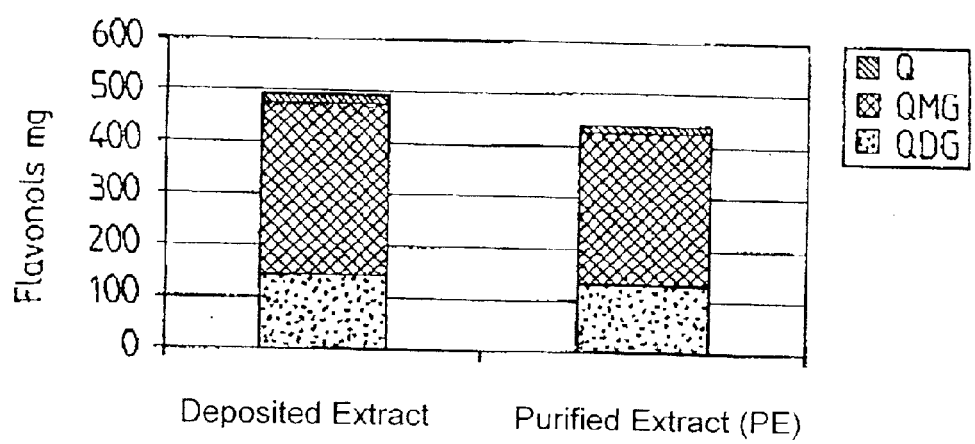
FIG. 4 shows flavonol contents.

FIG. 4 shows that the deposited extract contains 494 mg of phenolic compounds and the PE purified extract contains 449 mg of phenolic compounds. No qualitative difference is observed between the deposited extract and the onion PE purified extract, which contains more than 95% of quercetine derived flavonols comprising the following compounds: quercetine, quercetine monoglucoside and quercetine diglucoside amongst others.

The obtained values for the $T_A$, $T_E$ and $T_{NE}$ rates, as well as the quantity of the flavonols fixed by ml of resin are shown in table 3.

TABLE 3

| | PE |
|---|---|
| $T_A$ [%] | 99 |
| $T_E$ [%] | 91 |
| $T_{NE}$ [%] | 9 |
| Flavonol quantity fixed on the resin [mg/ml of resin] | 19.6 |

Table 3 shows that the rate of the flavonols adsorbed on the resin R according to the invention and recovered after methanol elution is high: 91% of the compounds are retained on the adsorbent and eluted by the methanol.

What is claimed is:

1. A method of obtaining a purified extract comprising polyphenolic compounds from a plant comprising polyphenolic compounds, the method comprising:
   extracting a plant material in order to obtain a raw plant material extract comprising polyphenolic compounds, wherein extracting comprises:
   (a) heating the plant material: and
   (b) submitting the plant material of step (a) to a vacuum:
   adsorbing the polyphenolic compounds contained in the extract on an adsorbing styrene-divinyl benzene resin that has a high adsorption performance and a high elution performance;
   eluting the polyphenolic compounds from the resin to obtain a purified extract comprising the polyphenolic compounds, and
   concentrating the purified extract;
   wherein the resin is further defined as having pores with an average size in the range from 50 to 110 angstroms, a surface area equal to or higher than 800 $m^2/g$ and a pore volume higher than 1 ml/g; and the plant material is all or part of a leafy plant of the Compositae family or a bulb plant of the Liliaceae family.

2. The method of claim 1, wherein the resin is further defined as having pores with an average size in the range 60 to 100 angstroms.

3. The method of claim 1, wherein the resin is further defined as having pores with an average size in the range 80 to 110 angstroms.

4. The method of claim 3, wherein the resin is further defined as having pores with an average size in the range 88 to 92 angstroms.

5. The method of claim 4, wherein the resin is further defined as having pores with an average size of about 90 angstroms.

6. The method of claim 1, wherein the resin is further defined as having a surface area equal to or higher than 880 $m^2/g$.

7. The method of claim 6, wherein the resin is further defined as having a surface area equal to or higher than 1000 m²/g.

8. The method of claim 7, wherein the resin is further defined as having a surface area equal to or higher than 1200 m²/g.

9. The method of claim 1, wherein the resin is further defined as having a pore volume equal to or higher than 1.4 ml/g.

10. The method of claim 9, wherein the resin is further defined as having a pore volume equal to or higher than 2 ml/g.

11. The method of claim 10, wherein the resin is further defined as having a pore volume equal to or higher than 2.4 ml/g.

12. The method of claim 1, wherein the resin is further defined as having the following physical features:
   pores with an average size in the range from 80 to 110 angstroms;
   a surface area equal to or higher than 1000 m²/g; and
   a pore volume equal to or higher than 2 ml/g.

13. The method of claim 12, wherein the resin is further defined as having the following physical features:
   pores with an average size of about 90 angstroms;
   a surface area equal to or higher 1200 m²/g; and
   a pore volume equal to or higher than 2.4 ml/g.

14. The method of claim 1, wherein the resin has an adsorption rate of polyphenolic compounds equal to or higher than 80% and an elution rate of polyphenolic compounds equal to or higher than 60%.

15. The method of claim 1, wherein the resin has the formula (I):

$$\text{(I)}$$

16. The method of claim 1, wherein submitting the plant material of step (a) to a vacuum produces a vapour, and wherein the vapour is condensed.

17. The method of claim 1, wherein the heating of step (a) occurs for less than fifteen minutes and without maceration.

18. The method of claim 1, wherein the heating of step (a) occurs in the absence of oxygen.

19. The method of claim 1, wherein the heating of step (a) is done with a condensing vapour.

20. The method of claim 1, wherein the heating of step (a) comprises circulating heated exudation juice or condensed vapour from a vacuum step to heat the plant material.

21. The method of claim 1, wherein the heating of step (a) comprises direct supply of heat to the plant material from a heat exchanger.

22. The method of claim 21, wherein the heat exchanger is a scraped surface heat exchanger.

23. The method of claim 1, wherein extracting is carried out in a continuous mode.

24. The method of claim 1, wherein extracting is carried out in a batch mode.

25. The method of claim 1, wherein eluting comprises use of a food solvent eluent.

26. The method of claim 25, wherein the food solvent eluent is ethanol or methanol.

27. The method of claim 1, wherein the purified extract has a polyphenolic compound content equal to or higher than 30% by weight.

28. The method of claim 1, further comprising drying the purified extract.

29. The method of claim 28, wherein the purified extract is spray-dried.

30. The method of claim 28, wherein the purified extract is freeze-dried.

31. The method of claim 1, wherein the purified extract is in a dry form.

32. The method of claim 31, wherein the dry form is further defined as a powder, granule, or ball form.

33. The method of claim 1, wherein the purified extract is in a liquid form.

34. The method of claim 1, wherein the plant is a leafy plant of the Compositae family selected from the group consisting of lettuce, endive, curly endive, and escarole.

35. The method of claim 34, wherein the plant is a lettuce selected from the group consisting of cos lettuce, batavia, and iceberg lettuce.

36. The method of claim 1, wherein the plant is a bulb plant of the Liliaceae family selected from the group consisting of onion, garlic, leek, and shallot.

37. The method claim 1, further comprising placing the purified extract in a cosmetic, food, or pharmaceutical.

38. The method of claim 1, wherein the resin is further defined as having:
   a pore volume equal to or higher than 1.4 ml/g;
   pores with an average size in the range 60 to 100 angstroms; and
   a surface area equal to or higher than 880 m²/g.

39. The method of claim 1, wherein the heating the plant material comprises heating at a temperature ranging from about 90° C. to about 105° C.

40. The method of claim 1, wherein submitting the plant material of step (a) to a vacuum comprises vacuuming at a pressure ranging from about $10^3$ to about $2 \times 10^4$ Pa.

* * * * *